United States Patent [19]

Saito

[11] Patent Number: 4,493,328

[45] Date of Patent: Jan. 15, 1985

[54] APPARATUS FOR TREATING SPASMODIC TORTICOLLIS

[76] Inventor: Iwao Saito, International House, 3701 Chestnut St., Philadelphia, Pa. 19014

[21] Appl. No.: 394,835

[22] Filed: Jul. 2, 1982

[51] Int. Cl.³ .............................................. A61B 5/10
[52] U.S. Cl. ............................... 128/782; 273/183 B; 340/573; 128/905
[58] Field of Search ............................... 340/573–576; 128/774, 782, 905; 273/DIG. 17, 190 R, 371, 183 B; 434/162, 258

[56] References Cited

U.S. PATENT DOCUMENTS

| | | | |
|---|---|---|---|
| 2,445,839 | 7/1948 | Newman et al. | 273/183 B X |
| 2,726,380 | 12/1955 | Campisi | 340/575 X |
| 3,524,030 | 8/1970 | Wiegel | 340/575 X |
| 3,629,594 | 12/1971 | Sandberg | 128/782 X |
| 3,699,856 | 10/1972 | Chabot et al. | 128/782 X |
| 4,392,830 | 7/1983 | Salzman et al. | 273/183 B X |

OTHER PUBLICATIONS

Halliday E. C. et al., "Aptitude Tester for Garment Workers", *Electronics*, Sep., 1947, pp. 90–92.

*Primary Examiner*—Kyle L. Howell
*Assistant Examiner*—Christine A. Fukushima
*Attorney, Agent, or Firm*—McGlew and Tuttle

[57] ABSTRACT

Apparatus for treating spasmodic torticollis comprises a light emitter for giving off a light beam, a fastener band for fastening the light-emitter on the head of a person being treated, a photosensor which is responsive to a light beam from the light emitter to change its output and a support for supporting the photosensor in a fixed position with respect to the chest of the person so that the photosensor may receive a light beam from the light emitter while the person holds his head in a mid position. The apparatus includes a switching circuit which responds to an output from the photosensor to control its output, an operant which responds to an output from the switching circuit to produce a rewarding effect, an accumulator which responds to the output from the switching circuit to produce an electrical signal directly proportional to the period during which the switching circuit is turned on, and a digital display which responds to an electrical signal from the accumulator to provide a digital reading of the total time period in a session during which the person has been able to hold his head in the mid position.

8 Claims, 2 Drawing Figures

APPARATUS FOR TREATING SPASMODIC TORTICOLLIS

FIELD AND BACKGROUND OF THE INVENTION

The present invention relates in general to so called "biofeedback" devices and in particular to a new and useful apparatus for treating spasmodic torticollis.

According to the article, "Biofeedback in the Treatment of Neuromuscular Disorders,38 by P. Engel-Sittenfeld, *Biofeedback and Behavior*, 1979, pp. 427–438, torticollis is a disturbance of movement and postural control of the head and neck, often associated with neck muscle spasms and relatively refractory to a wide variety of treatments, including analytical psychotherapy, surgical intervention, and various types of medication. Electromyograph feedback has been applied to this disturbance in a relatively large number of patients.

In 1973, Cleeland reported that ten patients were trained with a combination of electrical shock and EMG feedback whenever the muscle tension of their neck surpassed a certain threshold, which was progressively lowered. Eight of the ten patients showed a substantial reduction of spasmodic activity. In six, this improvement was stable for a mean follow-up period of 19 months. The author reported that eight patients improved when shock was added to the EMG feedback.

In 1974 and 1976, Brudny et al reported their approach to neuromuscular rehabilitation of 48 patients with torticollis, whereby the patients were taught how to relax and inhibit spastic activity and simultaneously try to increase the force of their atrophied muscles, a symptom combination that occurs frequently in torticollis, when one sternocleidomastoideus muscle is constantly tense while the opposite side of the neck is completely flaccid. 26 of the 48 cases achieved meaningful or major improvement in activities of daily living and partially a decrease of medication. During the follow-up from three months to three years, seven of the patients had regressed, leaving a success rate of about 40 percent. This promising result, however, was achieved with the patients sitting. Results under conditions of standing, walking or mental stress are not available at present.

SUMMARY OF THE INVENTION

It is an object of the invention to provide apparatus for treating spasmodic torticollis that can be used at home during a follow-up period, thereby not only preventing regression but also substituting for EMG feedback training.

It is another object of the invention to provide apparatus for treating spasmodic torticollis that can be used under conditions of standing, walking, or mental stress.

In accordance with the invention, there is provided apparatus for treating spasmodic torticollis, which comprises (a) means for emitting a beam of light;
(b) means for fastening the light-emitting means on the head of a person being treated;
(c) a photosensor which responds to a light beam from the light-emitting means to change its output;
(d) means for supporting the photosensor in a fixed position with respect to the chest of the person so that the photosensor may receive a light beam from the light-emitting means while the person holds his head in a mid position;
(e) a switching circuit which responds to an output from the photosensor to control the circuit output; and
(f) an operant which responds to an output from the switching circuit to produce a rewarding or negative reinforcement effect.

According to the invention, this apparatus may further comprise;

(g) an accumulator which responds to output from said switching circuit to produce an electrical signal which is directly proportional to the period during which the switching circuit is turned on; and
(h) a digital display which responds to an electrical signal from said accumulator to provide a digital reading of the total time period in a session during which the person has been able to hold his head in the mid-position.

This apparatus is so simple and compact that one can use it at home to train himself not only to maintain the improvement obtained from the EMG feedback training but also to learn how to relax and inhibit spastic activity and simultaneously try to increase the force of atrophied muscles. Since this apparatus may be fastened to the body, one can use it under conditions of standing, walking, or mental stress at home, office, etc.

Accordingly, a further object of the invention is to provide a device for treating spasmodic torticollis which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
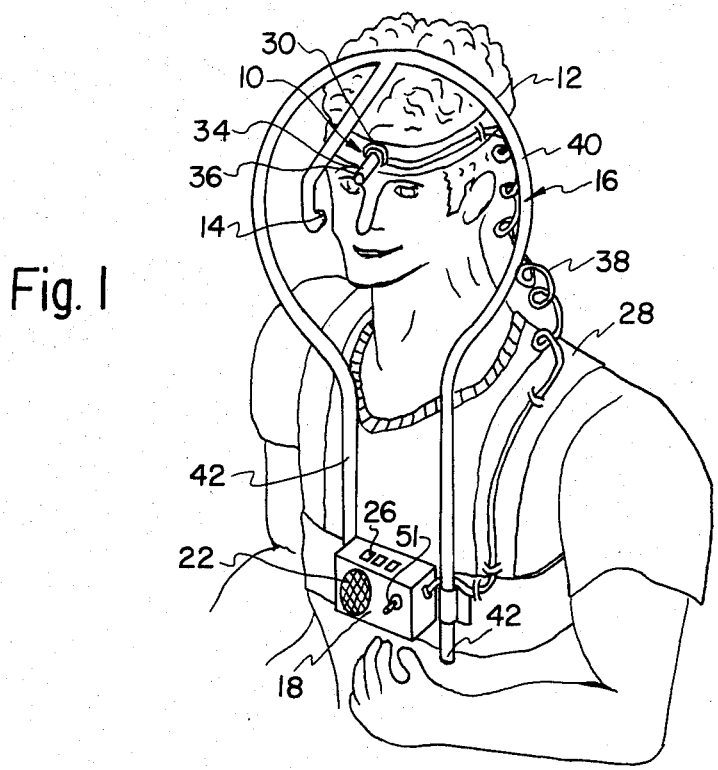
FIG. 1 is a perspective view of apparatus embodying the invention.

Referring to FIG. 1, there is shown apparatus for treating spasmodic torticollis according to the invention, which comprises a light emitter 10, a light emitter supporting band 12, a photosensor 14, a photosensor support 16, a signal processor 18 mainly comprising a switching circuit 20 (FIG. 2), an operant 22, an accumulator 24, and a digital display 26, and a processor support 28 designed to fasten the processor and the photosensor support to the chest of a person being treated. Photosensor 14 may be a photoresistor.

The light emitter 10 is made up of a base 30, a lamp 32 (not shown in FIG. 1), a cylinder 34, and a lens 36. The base 30 is secured to the band 12, which is detachably fastened to the head of a person to be treated. The lamp 32 is connected to the switching circuit 20 through a wire 38. The lamp may be replaced by another light emitting device such as a light emitting diode. The lens 36 and the cylinder 34 are adjusted so as to provide a proper beam of light.

The photosensor may be a photo conductor made of cadmium or a photo-cell. The photosensor support 16 is made up of a substantial loop section 40 and two legs 42 of a light metal such as aluminum. The ends of legs 42 are movably fixed to the support 28 so that the height of photosensor 14 may be adjusted. The angle of light emitter 10 in the vertical plane may be changed instead of or in addition to the adjustment by the photosensor support 16. A wire connecting the photosensor 14 and the switching circuit 20 is inserted through the hollow tube 16.

Figure 2:
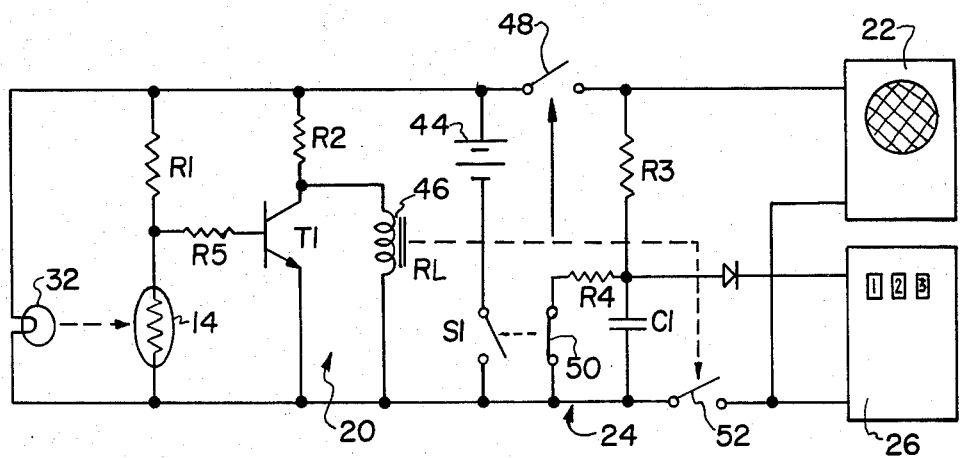
FIG. 2 is a schematic circuit diagram of the apparatus of FIG. 1.

Referring to FIG. 2, there is shown a circuit diagram of the signal processor 18 which comprises the switching circuit 20, the accumulator 24, the operant 22, and the digital display 26.

The switching circuit 20 is composed mainly of a transistor T1 and a relay RL and a power supply circuit which is made of a battery 44 and a switch S1, which are connected as shown in the diagram. The relay RL comprises an electromagnet 46 and switches 48 and 52.

The accumulator 24 is made up of a series circuit of a resistor R3 and a capacitor C1 and a discharge circuit of a resistor R4 and a switch 50. The switch 50 is associated with the switch S1 so that when the switch S1 is closed, the switch 50 is opened to allow charging the capacitor C1 with the time constant which is determined by the product of R3 and C1.

The digital display 26 may be any device which is able to convert an analog signal to a digital display. The operant 22 may be a radio receiver, TV set, or any other device which is able to produce rewarding effects or negative reinforcement such as an electric shock.

In operation, when an operator closes the switch S1, the light emitter 10 gives off a light beam and the switching circuit 20 is energized. If the operator has left spasmodic torticollis with spasm of the right sternocleidomastoid muscle, with his neck turning to the left, the light beam fails to hit the photosensor 14. The resistance of photo conductor 14 is so large that the transistor T1 is turned on, thus holding the electromagnet 46 unactuated and the switch 48 open. Consequently, the operant 22 is turned off and does not produce any rewarding effect for the operator. Photosensor 14 is in series with resistor R1 for receiving part of the voltage of battery 44.

If the operator is able to release his spasm and bring the neck back to the mid position, the light beam hits the photosensor 14 reducing the resistance much lower than the value of the resistor R5, with the result that the transistor T1 is turned off, thus energizing the electromagnet 46 to close the switch 48. As soon as the switch 48 is closed, the operant is actuated to produce rewarding effects and the capacitor C1 is charged to build up a voltage, the magnitude of which is proportional to the period during which the switch 48 is closed and in turn the operator holds his head in the mid position. The digital display 26 converts this voltage into a digital display of time.

After a while, if the right sternocleidomastoid muscle is in severe spasm and the neck rotated to the left, the light beam misses the photosensor 14 thereby opening the switches 48 and 52, which holds the voltage across the capacitor C1 and enables the capacitor to build up a voltage from the existing level when it is charged the next time. The voltage across the capacitor is accumulated for the period of a session which is usually from 10 to 15 minutes. At the end of a session, the digital display 26 provides the total time period during which the operator has been able to hold his head in the midline for the period of a session. When the switch S1 is opened, the switch 50 is closed to discharge the capacitor C1 through the resistor R4, thus resetting the accumulator 24.

The position of the light source 10 and photosensor 14 can be reversed. Also, the chest connection for the photosensor or light source may be replaced by any other fixed connection to the person's trunk which can present a fixed frame of reference with respect to the person's head.

While a specific embodiment of the invention has been shown and described in detail to illustrate the application of the principles of the invention, it will be understood that the invention may be embodied otherwise without departing from such principles.

What is claimed is:

1. An apparatus for treating spasmodic torticollis, comprising:

means for emitting a beam of light;

means for fastening said light emitting means to the head of a person being treated;

a photosensor which responds to a light beam from said light emitting means to change an output thereof;

means adapted to be attached to the trunk of a person for supporting said photosensor in a fixed position with respect to the trunk of the person so that said photosensor may receive a light beam from said light emitting means while the person holds his head in a mid position;

a switching circuit connected to said photosensor, which responds to an output from said photosensor to control a circuit output thereof;

an operant connected to said circuit, which responds to the output from said switching circuit to produce an effect on the person;

an accumulator connected to said circuit, which responds to the output from said switching circuit to produce an electrical signal which is directly proportional to the time period during which said switching circuit is producing the circuit output; and display means connected to said accumulator which responds to an electrical signal from said accumulator to provide a display indicative of the total time period during which the person has been able to hold his head in the mid position.

2. An apparatus for treating spasmodic torticollis according to claim 1, wherein said operant is a radio receiver.

3. An apparatus for treating spasmodic torticollis according to claim 1, wherein said display means is a digital display that is able to provide a digital reading of the total time period during which said person has been able to hold his head in the mid position.

4. An apparatus according to claim 1, wherein said accumulator comprises an RC circuit having a capacitor which is charged during the time period, said photosensor having a first output when a light beam from said light emitting means shines thereon and a second output when the light beam from said light emitting means does not shine thereon, said switching circuit including a relay and a switch connected to said relay which is closed by said relay for charging said capacitor, said relay operable to close said switch when said photosensor produces said first output.

5. An apparatus for treating spasmodic torticollis according to claim 4, wherein said switching circuit includes a switching transistor and a battery, said photosensor comprising a photoresistor connected to a base of said switching transistor, said battery connected to said base of said switching transistor and said relay connected across the emitter and collector of said switching transistor.

6. An apparatus for treating spasmodic torticollis according to claim 5, including a discharging switch connected across said capacitor and an activating switch connected to said battery and connected to said discharging switch, said activating switch being closed with said discharging switch being open and said discharging switch being closed with said activating switch being open so that upon disconnection of said battery by the opening of said activating switch, said discharging switch is closed to discharge said capacitor.

7. An apparatus for treating spasmodic torticollis according to claim 6, wherein said light emitting means comprises a lamp connected across said battery and activating switch.

8. A method of treating spasmodic torticollis comprising:
 attaching a source of light to a patient's head;
 attaching a light sensor to the patient's trunk for receiving light from the light source when the patient's head is in a mid position; and
 activating an operant for producing an effect on the patient when the light from the light source is not received by the light sensor.

* * * * *